US009239522B2

United States Patent
Shih et al.

(10) Patent No.: US 9,239,522 B2
(45) Date of Patent: Jan. 19, 2016

(54) METHOD OF DETERMINING AN ASYMMETRIC PROPERTY OF A STRUCTURE

(75) Inventors: Meng-Fu Shih, San Jose, CA (US); In-Kyo Kim, Cupertino, CA (US); Xiafang Zhang, San Jose, CA (US); Leonid Poslavsky, Belmont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 1091 days.

(21) Appl. No.: 12/900,863

(22) Filed: Oct. 8, 2010

(65) Prior Publication Data

US 2012/0086940 A1    Apr. 12, 2012

(51) Int. Cl.
| | |
|---|---|
| *G01J 3/36* | (2006.01) |
| *G01B 11/30* | (2006.01) |
| *G01N 21/00* | (2006.01) |
| *G03F 7/20* | (2006.01) |
| *G01N 21/47* | (2006.01) |
| *G01N 21/956* | (2006.01) |
| *G01N 21/21* | (2006.01) |
| *G01N 21/95* | (2006.01) |

(52) U.S. Cl.
CPC .......... *G03F 7/70616* (2013.01); *G01N 21/211* (2013.01); *G01N 21/47* (2013.01); *G01N 21/4788* (2013.01); *G01N 21/956* (2013.01); *G01B 2210/56* (2013.01); *G01N 21/9501* (2013.01); *G01N 2021/213* (2013.01); *G01N 2201/1296* (2013.01)

(58) Field of Classification Search
CPC ... G01N 21/17; G01N 21/47; G01N 21/9501; G01N 21/956
See application file for complete search history.

(56) References Cited

U.S. PATENT DOCUMENTS

| | | | |
|---|---|---|---|
| 6,462,818 B1 * | 10/2002 | Bareket ..................... | 356/401 |
| 7,428,060 B2 | 9/2008 | Jin et al. | |
| 2002/0135781 A1 | 9/2002 | Singh et al. | |
| 2004/0257588 A1 * | 12/2004 | Shchegrov et al. .......... | 356/601 |
| 2004/0267397 A1 | 12/2004 | Doddi et al. | |
| 2005/0041258 A1 * | 2/2005 | Opsal et al. ................ | 356/601 |
| 2007/0075688 A1 * | 4/2007 | Aemireddy et al. ......... | 323/234 |
| 2007/0201043 A1 | 8/2007 | Raymond | |

(Continued)

FOREIGN PATENT DOCUMENTS

| | | |
|---|---|---|
| CN | 1041035 | 4/1990 |
| CN | 1879004 | 12/2006 |

(Continued)

OTHER PUBLICATIONS

International Search Report and Written Opinion from PCT/US2011/055163 mailed May 2, 2012, 11 pgs.

(Continued)

*Primary Examiner* — Gregory J Toatley
*Assistant Examiner* — Hina F Ayub
(74) *Attorney, Agent, or Firm* — Blakely Sokoloff Taylor & Zafman LLP

(57) ABSTRACT

Methods of determining asymmetric properties of structures are described. A method includes measuring, for a grating structure, a first signal and a second, different, signal obtained by optical scatterometry. A difference between the first signal and the second signal is then determined. An asymmetric structural parameter of the grating structure is determined based on a calculation using the first signal, the second signal, and the difference.

16 Claims, 12 Drawing Sheets

(56) References Cited

U.S. PATENT DOCUMENTS

2007/0223011 A1    9/2007  Jin et al.
2009/0027691 A1*   1/2009  Van Der Schaar et al. ... 356/612
2010/0328665 A1*  12/2010  Kaye et al. .................... 356/342

FOREIGN PATENT DOCUMENTS

| JP | 2003-224057 | 8/2003 |
|----|-------------|--------|
| JP | 2007-505322 | 3/2007 |
| KR | 102007001621 | 2/2007 |
| WO | WO 2005/028992 | 3/2005 |

OTHER PUBLICATIONS

International Preliminary Report on Patentability from PCT/US2011/055163 mailed Apr. 18, 2013, 7 pgs.
First Office Action dated May 21, 2015 (+ English translation), in Chinese Patent Application No. 201180048788.8, 31 pages.
Notice of Reasons for Refusal mailed Sep. 1, 2015 (+ English translation), in Japanese Patent Application No. 2013-532956, 5 pages.

\* cited by examiner

METHOD OF DETERMINING AN ASYMMETRIC PROPERTY OF A STRUCTURE

TECHNICAL FIELD

Embodiments of the present invention are in the field of optical metrology, and, more particularly, relate to methods of determining asymmetric properties of structures.

BACKGROUND

For the past several years, a rigorous couple wave approach (RCWA) and similar algorithms have been widely used for the study and design of diffraction structures. In the RCWA approach, the profiles of periodic structures are approximated by a given number of sufficiently thin planar grating slabs. Specifically, RCWA involves three main steps, namely, the Fourier expansion of the field inside the grating, calculation of the eigenvalues and eigenvectors of a constant coefficient matrix that characterizes the diffracted signal, and solution of a linear system deduced from the boundary matching conditions. RCWA divides the problem into three distinct spatial regions: 1) the ambient region supporting the incident plane wave field and a summation over all reflected diffracted orders, 2) the grating structure and underlying non-patterned layers in which the wave field is treated as a superposition of modes associated with each diffracted order, and 3) the substrate containing the transmitted wave field.

The accuracy of the RCWA solution depends, in part, on the number of terms retained in the space-harmonic expansion of the wave fields, with conservation of energy being satisfied in general. The number of terms retained is a function of the number of diffraction orders considered during the calculations. Efficient generation of a simulated diffraction signal for a given hypothetical profile involves selection of the optimal set of diffraction orders at each wavelength for both transverse-magnetic (TM) and/or transverse-electric (TE) components of the diffraction signal. Mathematically, the more diffraction orders selected, the more accurate the simulations. However, the higher the number of diffraction orders, the more computation is required for calculating the simulated diffraction signal. Moreover, the computation time is a nonlinear function of the number of orders used.

SUMMARY

Embodiments of the present invention include methods of determining asymmetric properties of structures.

In an embodiment, a method includes measuring, for a grating structure, a first signal and a second, different, signal obtained by optical scatterometry. The method also includes determining a difference between the first signal and the second signal. The method also includes determining an asymmetric structural parameter of the grating structure based on a calculation using the first signal, the second signal, and the difference.

In another embodiment, a machine-accessible storage medium has instructions stored thereon which cause a data processing system to perform a method of determining an asymmetric property of a structure. The method includes measuring, for a grating structure, a first signal and a second, different, signal obtained by optical scatterometry. The method also includes determining a difference between the first signal and the second signal. The method also includes determining an asymmetric structural parameter of the grating structure based on a calculation using the first signal, the second signal, and the difference.

DETAILED DESCRIPTION

Figure 1:
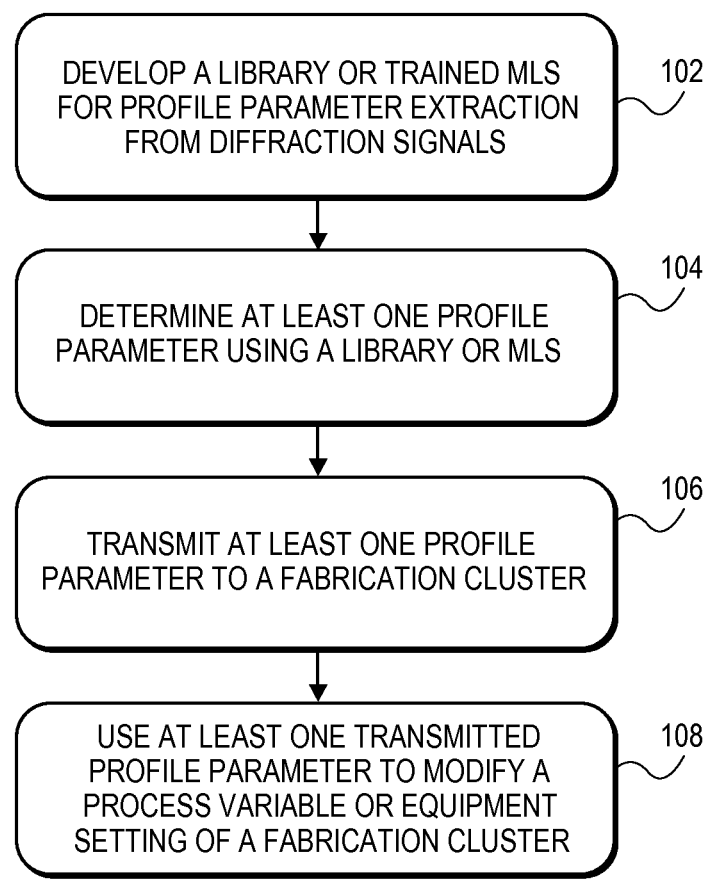
FIG. 1 depicts a flowchart representing an exemplary series of operations for determining and utilizing structural parameters for automated process and equipment control, in accordance with an embodiment of the present invention.

Methods of determining asymmetric properties of structures are described herein. In the following description, numerous specific details are set forth, such as examples of asymmetric properties of structures, in order to provide a thorough understanding of embodiments of the present invention. It will be apparent to one skilled in the art that embodiments of the present invention may be practiced without these specific details. In other instances, well-known processing steps, such as fabricating stacks of patterned material layers, are not described in detail in order to not unnecessarily obscure embodiments of the present invention. Furthermore, it is to be understood that the various embodiments shown in the figures are illustrative representations and are not necessarily drawn to scale.

Disclosed herein are methods of determining asymmetric properties of structures. In one embodiment, a method includes measuring, for a grating structure, a first signal and a second, different, signal obtained by optical scatterometry. A difference between the first signal and the second signal is then determined. An asymmetric structural parameter of the grating structure is determined based on a calculation using the first signal, the second signal, and the difference. In accordance with an embodiment of the present invention, and in contrast to conventional approaches, by including the difference in the calculation, the asymmetry of the measured structure is retained as opposed to being averaged to provide an otherwise non-representative asymmetric structure simulation.

Orders of a diffraction signal may be simulated as being derived from a periodic structure. The zeroth order represents a diffracted signal at an angle equal to the angle of incidence of a hypothetical incident beam, with respect to the normal N of the periodic structure. Higher diffraction orders are designated as +1, +2, +3, −1, −2, −3, etc. Other orders known as evanescent orders may also be considered. In accordance with an embodiment of the present invention, a simulated diffraction signal is generated for use in optical metrology. For example, profile parameters, such as structural sidewall angles, may be modeled for use in optical metrology. Optical properties of materials, such as index of refractivity and coefficient of extinction, (n & k), in wafer structures may also be modeled for use in optical metrology.

In accordance with an embodiment of the present invention, a correlation among different critical dimension (CD) parameters for scatterometry signals is reduced, or the sensitivity of these parameters is increased, by obtaining an asymmetry property of a semiconductor device structures. This approach may improve the accuracy of CD measurements using regression or optimization methods. For example, conventional methods in scatterometry CD measurements use regression or optimization methods to find optimal CD parameters by matching modeling scatterometer signals to the signals measured from a single or multiple azimuth angles. A disadvantage of such a conventional approach is the inability to break correlation between the same (or similar) type of CD parameters in different locations of asymmetric semiconductor devices. For example, for a trapezoid grating with asymmetric left and right wall angles or asymmetric left and right spacer widths, conventional methods have almost full correlation between the two wall angles or the two spacer widths at the left and right sides of the trapezoids. Therefore, those highly correlated CD parameters cannot be accurately measured using conventional optical scatterometry measurements.

As semiconductor device features scale smaller, the device structure becomes significantly more complicated. For example, the potential misalignment in the lithographic and etch processes may need to be monitored. In accordance with an embodiment of the present invention, differences of scatterometer signals measured at different azimuth (Az) angles or different angles of incidence (AOI) are included in the regression or optimization of CD parameters to obtain more information about the asymmetry property of the device structure. Therefore, asymmetric features such as the left and right wall angles or the left and right spacer widths in the geometry profile may be more accurately measured.

An asymmetric factor can be defined based on the differential signal to measure the degree of asymmetry for a given structure. For example, in one embodiment, a possible definition is the mean squared magnitude of the differential signal, according to eq. 1:

$$\text{Asymmetric Factor } \eta = \sum_{i=1}^{n} d_i^2 \qquad (\text{eq. 1})$$

where $d_i$ is the differential signal with i=1, . . . , n.

Calculations based simulated diffraction orders may be indicative of profile parameters for a patterned film, such as a patterned semiconductor film or photo-resist layer, and may be used for calibrating automated processes or equipment control. FIG. 1 depicts a flowchart 100 representing an exemplary series of operations for determining and utilizing structural parameters, such as profile parameters, for automated process and equipment control, in accordance with an embodiment of the present invention.

Referring to operation 102 of flowchart 100, a library or trained machine learning systems (MLS) is developed to extract profile parameters from a set of measured diffraction signals. In operation 104, at least one profile parameter of a structure is determined using the library or the trained MLS. In operation 106, the at least one profile parameter is transmitted to a fabrication cluster configured to perform a processing step, where the processing step may be executed in the semiconductor manufacturing process flow either before or after measurement step 104 is made. In operation 108, the at least one transmitted profile parameter is used to modify a process variable or equipment setting for the processing step performed by the fabrication cluster.

For a more detailed description of machine learning systems and algorithms, see U.S. patent application Ser. No. 10/608,300, entitled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety. For a description of diffraction order optimization for two dimensional repeating structures, see U.S. patent application Ser. No. 11/388,265, entitled OPTIMIZATION OF DIFFRACTION ORDER SELECTION FOR TWO-DIMENSIONAL STRUCTURES, filed on Mar. 24, 2006, which is incorporated herein by reference in its entirety.

Figure 2:
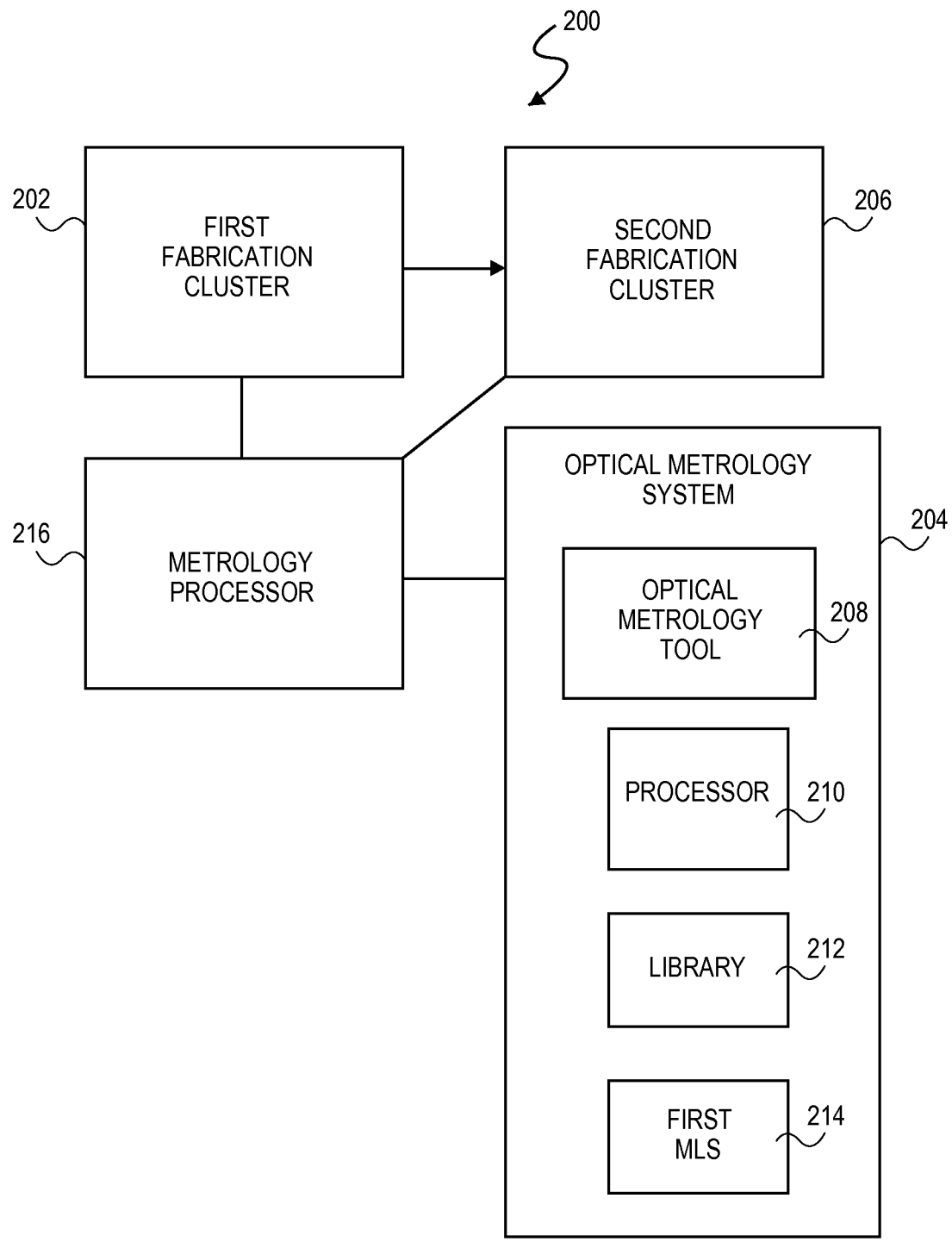
FIG. 2 is an exemplary block diagram of a system for determining and utilizing structural parameters for automated process and equipment control, in accordance with an embodiment of the present invention.

FIG. 2 is an exemplary block diagram of a system 200 for determining and utilizing structural parameters, such as profile parameters, for automated process and equipment control, in accordance with an embodiment of the present invention. System 200 includes a first fabrication cluster 202 and optical metrology system 204. System 200 also includes a second fabrication cluster 206. Although the second fabrication cluster 206 is depicted in FIG. 2 as being subsequent to first fabrication cluster 202, it should be recognized that second fabrication cluster 206 can be located prior to first fabrication cluster 202 in system 200 (and, e.g., in the manufacturing process flow).

A photolithographic process, such as exposing and developing a photo-resist layer applied to a wafer, can be performed using first fabrication cluster 202. In one exemplary embodiment, optical metrology system 204 includes an optical metrology tool 208 and processor 210. Optical metrology tool 208 is configured to measure a diffraction signal obtained from the structure. If the measured diffraction signal and the simulated diffraction signal match, one or more values of the profile parameters are determined to be the one or more values of the profile parameters associated with the simulated diffraction signal.

In one exemplary embodiment, optical metrology system 204 can also include a library 212 with a plurality of simulated diffraction signals and a plurality of values of one or more profile parameters associated with the plurality of simulated diffraction signals. As described above, the library can be generated in advance. Metrology processor 210 can compare a measured diffraction signal obtained from a structure to the plurality of simulated diffraction signals in the library. When a matching simulated diffraction signal is found, the one or more values of the profile parameters associated with the matching simulated diffraction signal in the library is assumed to be the one or more values of the profile parameters used in the wafer application to fabricate the structure.

System 200 also includes a metrology processor 216. In one exemplary embodiment, processor 210 can transmit the one or more values of the one or more profile parameters to metrology processor 216. Metrology processor 216 can then adjust one or more process parameters or equipment settings of first fabrication cluster 202 based on the one or more values of the one or more profile parameters determined using optical metrology system 204. Metrology processor 216 can also adjust one or more process parameters or equipment settings of the second fabrication cluster 206 based on the one or more values of the one or more profile parameters determined using optical metrology system 204. As noted above, fabrication cluster 206 can process the wafer before or after fabrication cluster 202. In another exemplary embodiment, processor 210 is configured to train machine learning system 214 using the set of measured diffraction signals as inputs to machine learning system 214 and profile parameters as the expected outputs of machine learning system 214.

Figure 3:
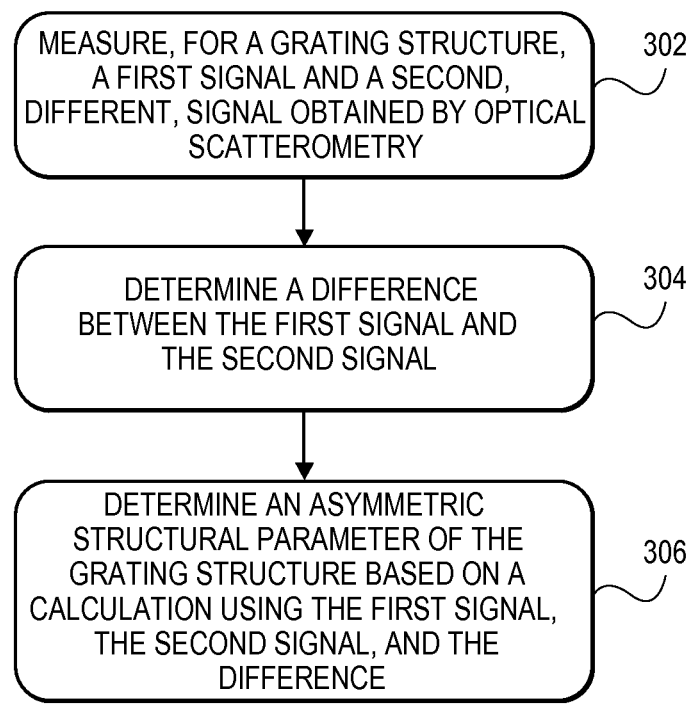
FIG. 3 depicts a flowchart representing operations in a method of determining an asymmetric property of a structure, in accordance with an embodiment of the present invention.

In an aspect of the present invention, asymmetry in a structure is determined based on calculations using measurements from optical metrology of the structure. For example, FIG. 3 depicts a flowchart 300 representing operations in a method of determining an asymmetric property of a structure, in accordance with an embodiment of the present invention.

Referring to operation 302 of flowchart 300, a method of determining an asymmetric property of a structure includes measuring, for a grating structure, a first signal and a second, different, signal obtained by optical scatterometry.

In accordance with an embodiment of the present invention, the first signal and the second signal are measured at first and second azimuth angles, respectively, of the grating structure. In another embodiment, the first signal and the second signal are measured at first and second angles of incidence, respectively, of the grating structure. In another embodiment, the first signal and the second signal are measured at first and second polarizer/analyzer angles, respectively, of the grating structure. In another embodiment, the first signal and the second signal are measured for first and second measurement targets, respectively, of the grating structure. In an embodiment, the optical scatterometry is a technique such as, but not limited to, optical spectroscopic ellipsometry (SE), beam profile reflectometry (BPR), and enhanced ultra-violet reflectrometry (eUVR).

Figure 4A:
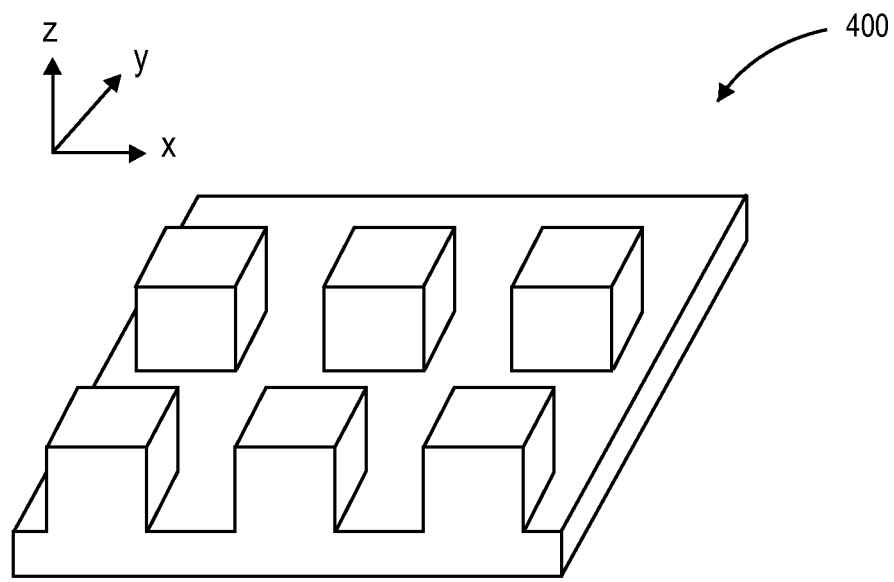
FIG. 4A depicts a periodic grating having a profile that varies in the x-y plane, in accordance with an embodiment of the present invention.

In an embodiment, measuring the first and second signals for the grating structure includes using a three-dimensional grating structure. The term "three-dimensional grating structure" is used herein to refer to a structure having an x-y profile that varies in two dimensions in addition to a depth in the z-direction. For example, FIG. 4A depicts a periodic grating 400 having a profile that varies in the x-y plane, in accordance with an embodiment of the present invention. The profile of the periodic grating varies in the z-direction as a function of the x-y profile.

Figure 4B:
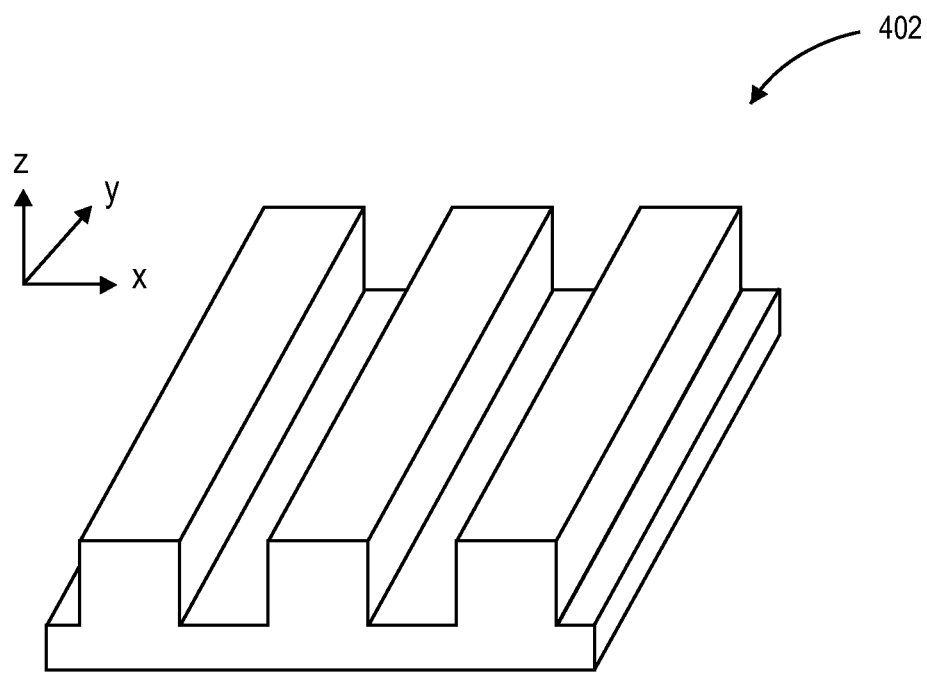
FIG. 4B depicts a periodic grating having a profile that varies in the x-direction but not in the y-direction, in accordance with an embodiment of the present invention.

In an embodiment, measuring the first and second signals for the grating structure includes using a two-dimensional grating structure. The term "two-dimensional grating structure" is used herein to refer to a structure having an x-y profile that varies in only one dimension in addition to a depth in the z-direction. For example, FIG. 4B depicts a periodic grating 402 having a profile that varies in the x-direction but not in the y-direction, in accordance with an embodiment of the present invention. The profile of the periodic grating varies in the z-direction as a function of the x profile. It is to be understood that the lack of variation in the y-direction for a two-dimensional structure need not be infinite, but any breaks in the pattern are considered long range, e.g., any breaks in the pattern in the y-direction are spaced substantially further apart than the brakes in the pattern in the x-direction.

Referring to operation 304 of flowchart 300, the method of determining the asymmetric property of the structure also includes determining a difference between the first signal and the second signal. For example, in an embodiment, a difference is taken between two like signals, such as a difference between two different azimuth angle measurements or a difference between two different angle of incidence measurements.

Referring to operation 306 of flowchart 300, the method of determining the asymmetric property of the structure also includes determining an asymmetric structural parameter of the grating structure based on a calculation using the first signal, the second signal, and the difference.

In accordance with an embodiment of the present invention, the asymmetric structural parameter is a sidewall angle, and wherein the grating structure has a first sidewall with a first sidewall angle and a second sidewall with a second, different, sidewall angle. In an embodiment, the asymmetric structural parameter is one such as, but not limited to, top corner roundings, bottom footings, or critical dimension (CD) pitch shifts. In an embodiment, the grating structure is composed of a first material and further includes sidewall spacers composed of a second, different material, and wherein the asymmetric structural parameter is one such as, but not limited to, sidewall spacer width or sidewall spacer height. In a specific embodiment, the sidewalls each include only a single sidewall spacer. However, in another specific embodiment, the sidewalls each include two or more sidewall spacers. In another embodiment, the asymmetric structural parameter is a grating structure composed of a first material and further including left and right sidewall spacers composed of a second and a third different materials, respectively.

In an embodiment, the calculation is a regression calculation. In one such embodiment, determining the structural parameter further includes simultaneously using one or more non-differential signals in the calculation, the one or more non-differential signals is one such as, but not limited to, azimuth angles, angles of incidence, polarizer/analyzer angles, or additional measurement targets.

In an embodiment, the method of determining the asymmetric property of the structure further includes altering parameters of a process tool based on the asymmetric structural parameter by using a technique such as, but not limited to, a feedback technique, a feed-forward technique, and an in situ control technique. In an embodiment, the asymmetric factor can be used to more accurately set up a device structure profile and geometry in a CD metrology tool recipe. For example, if the asymmetric factor is smaller than a provided threshold, e.g., tool noise level, then the structure may be modeled by a symmetric profile. Otherwise, in an embodiment, the profile is asymmetric with the degree of asymmetry corresponding to the asymmetric factor. In an embodiment, the differential signal and the asymmetric factor is used as a part of CD metrology tool validation, diagnostic and characterization by measuring a "known" symmetric structure. The asymmetric factor is used to determine the tool effect which needs to be less than a predetermined specification quantity for future applicability to generic asymmetric structure measurements.

In accordance with an embodiment of the present invention, the method of determining the asymmetric property of the structure further includes comparing a simulated spectrum to a sample spectrum. In one embodiment, a set of diffraction orders is simulated to represent diffraction signals from a three-dimensional grating structure generated by an ellipsometric optical metrology system, such as the optical metrology system 1500 described below in association with FIG. 15. However, it is to be understood that the same concepts and principles equally apply to the other optical metrology systems, such as reflectometric systems. The diffraction signals represented may account for features of the three-dimensional grating structure such as, but not limited to, profile, dimensions or material composition.

Figure 5:
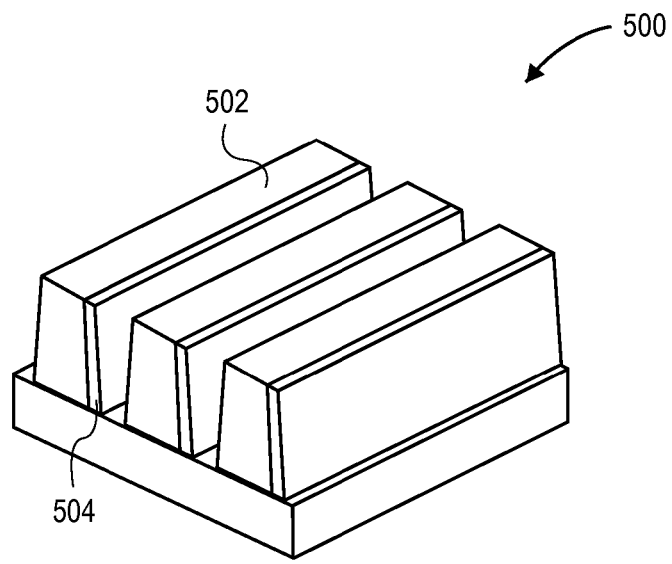
FIG. 5 illustrates an angled view of a structure with asymmetric left and right spacer widths, in accordance with an embodiment of the present invention.
Figure 6:
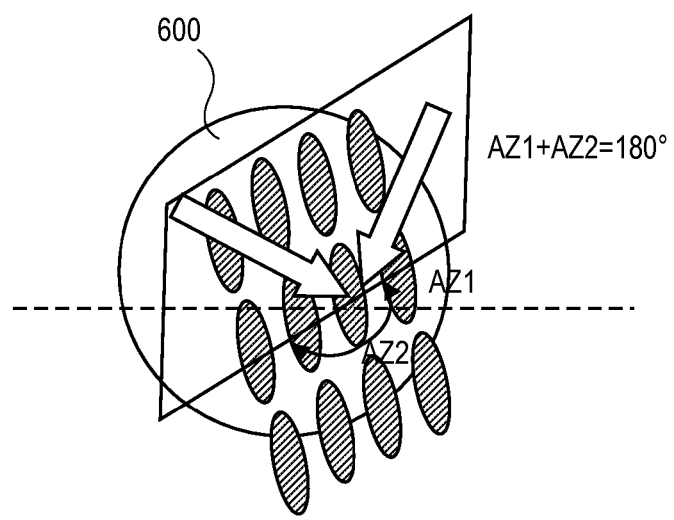
FIG. 6 illustrates a top-down plan view of a wafer, having the structure of FIG. 5 thereon, measured at a first azimuth angle (AZ1) and then rotated by 180 degrees to be measured at a second azimuth angle (AZ2), in accordance with an embodiment of the present invention.
Figure 7:
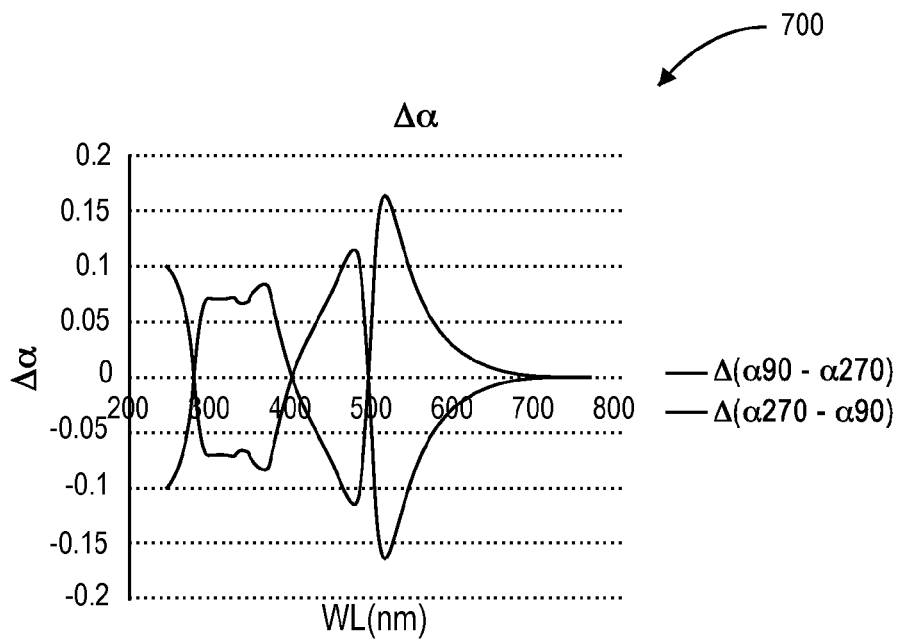
FIG. 7 illustrates a plot representing calculations based on the difference determined between the first azimuth angle (AZ1) measurement and the second azimuth angle (AZ2) measurement from FIG. 6, in accordance with an embodiment of the present invention.
Figure 8:
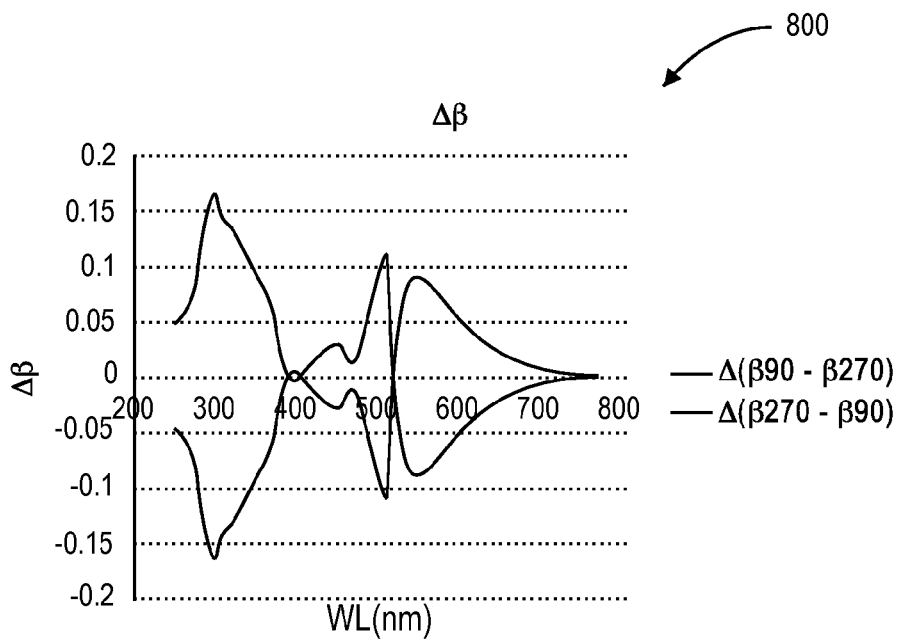
FIG. 8 illustrates a plot representing calculations based on the difference determined between the first azimuth angle (AZ1) measurement and the second azimuth angle (AZ2) measurement from FIG. 6, in accordance with an embodiment of the present invention.

Details of operation of the above described method are illustrated in the following examples. In a first example, in accordance with an embodiment of the present invention, a structure 500 with asymmetric left and right spacer widths is provided, as depicted in FIG. 5. Specifically, for illustrative purposes, referring to FIG. 5, each central structure 502 has a thin spacer layer 504 on its right sidewall. A wafer 600 having structure 500 is measured at a first azimuth angle (AZ1) and then rotated by 180 degrees to be measured at a second azimuth angle (AZ2), as depicted in FIG. 6. The signal difference is be calculated based on these two measurements, as shown in plots 700 and 800 of FIGS. 7 and 8, respectively. The asymmetric factor can be defined according to eq. 2:

$$\eta = \sum_{i=1}^{n} \Delta\alpha^2(\lambda_i) + \sum_{i=1}^{n} \Delta\beta^2(\lambda_i) \quad \text{(eq. 2)}$$

In a specific embodiment of the first example, the central structure is composed of silicon, while the sidewall spacers are composed of silicon oxide or silicon dioxide. The structure is measured in two opposite directions. If the sidewall thicknesses are equal, e.g. if the structure is symmetric with respect to spacer sidewall thickness, then the calculated difference between the two measurements is zero. However, if the spacer sidewall thicknesses differ, leading to an asymmetric structure, then the difference between the two measurements is non-zero, providing an offset. The calculated offset is then included in an optical metrology measurement or simulation, or both, to provide a more realistic indication of the structural profile of the measured device.

Figure 9:
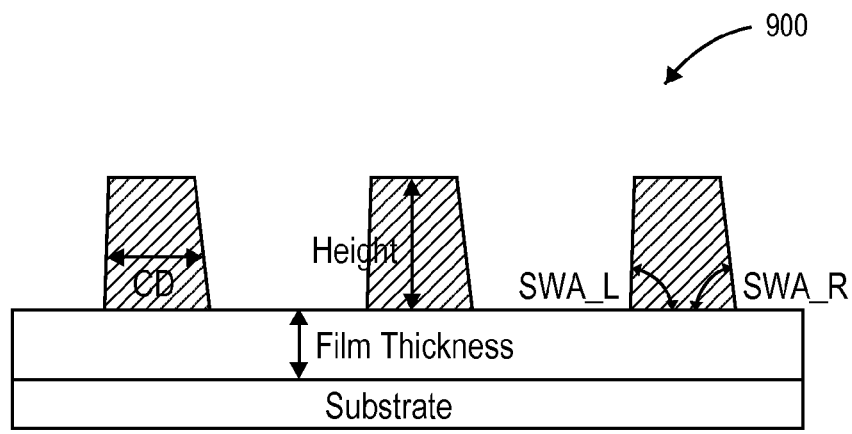
FIG. 9 illustrates an asymmetric grating target with different left and right wall angles, in accordance with an embodiment of the present invention.
Figure 10:
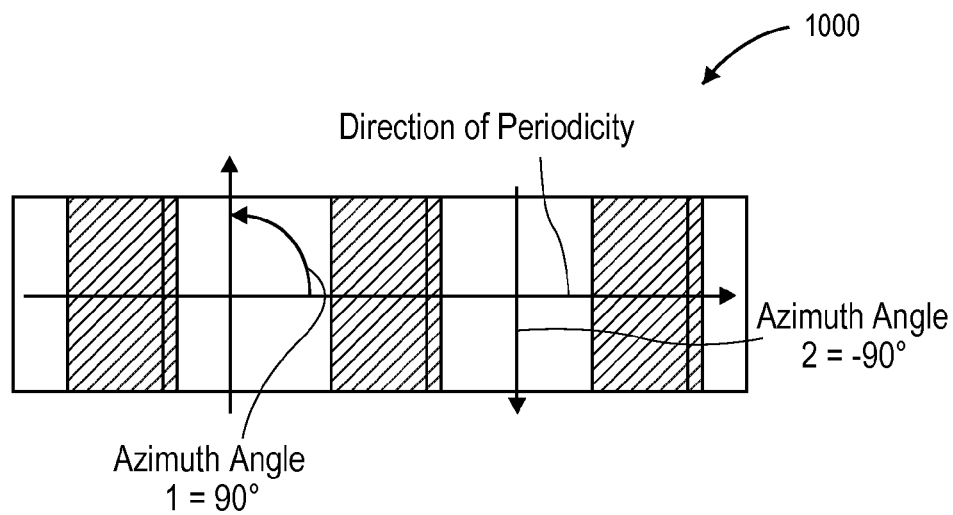
FIG. 10 illustrates a top-down view of the grating target of FIG. 9, along with the azimuth angle of measurement, in accordance with an embodiment of the present invention.

In a second example, in accordance with an embodiment of the present invention, an asymmetric grating target 900 with different left and right wall angles is provided, as depicted in FIG. 9. Referring to FIG. 9, the parameters measured by the scatterometer include critical dimension (CD), height, film thickness, left sidewall angle (SWA_L), and right sidewall angle (SWA_R). The azimuth angle of the measurement is defined as the top-down view of the grating target 900, as depicted in FIG. 10, where the azimuth angle's value is defined as counter-clockwise positive.

Referring again to FIGS. 9 and 10, a conventional approach would typically measure target 900 or 1000, respectively, at 0 degree azimuth angle since the approach exhibits good sensitivity to all of the above listed parameters. Then, regression would be used to find the optimal values of these parameters that minimize the distance (defined by some cost function) between the theoretically calculated model spectra and the measured spectra. However, the regression results are usually not accurate because the sensitivities of SWA_L and SWA_R are almost fully corrected. Additionally, the conventional approach would likely include measuring the target at 90 (or −90) degree azimuth angle and using these spectra alone or together with the 0 degree azimuth angle spectra in the regression. This approach is used because the sensitivities of SWA_L and SWA_R are slightly less correlated in the 90 (or −90) degree azimuth angle spectra. However, the decrease in correlation is very small and it does not significantly help in the measurement accuracy.

Figure 11:
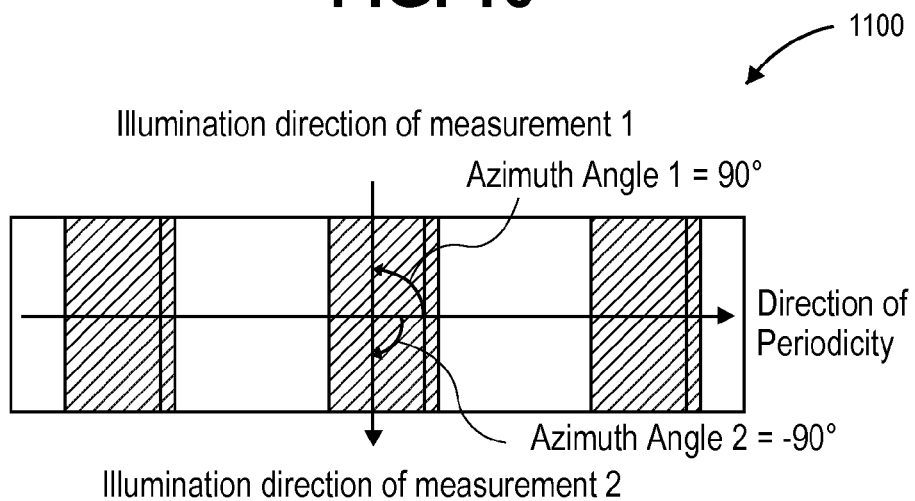
FIG. 11 illustrates a top-down view of the grating target of FIG. 9, along with azimuth measurements made at 90 and −90 degrees, in accordance with an embodiment of the present invention.
Figure 12:
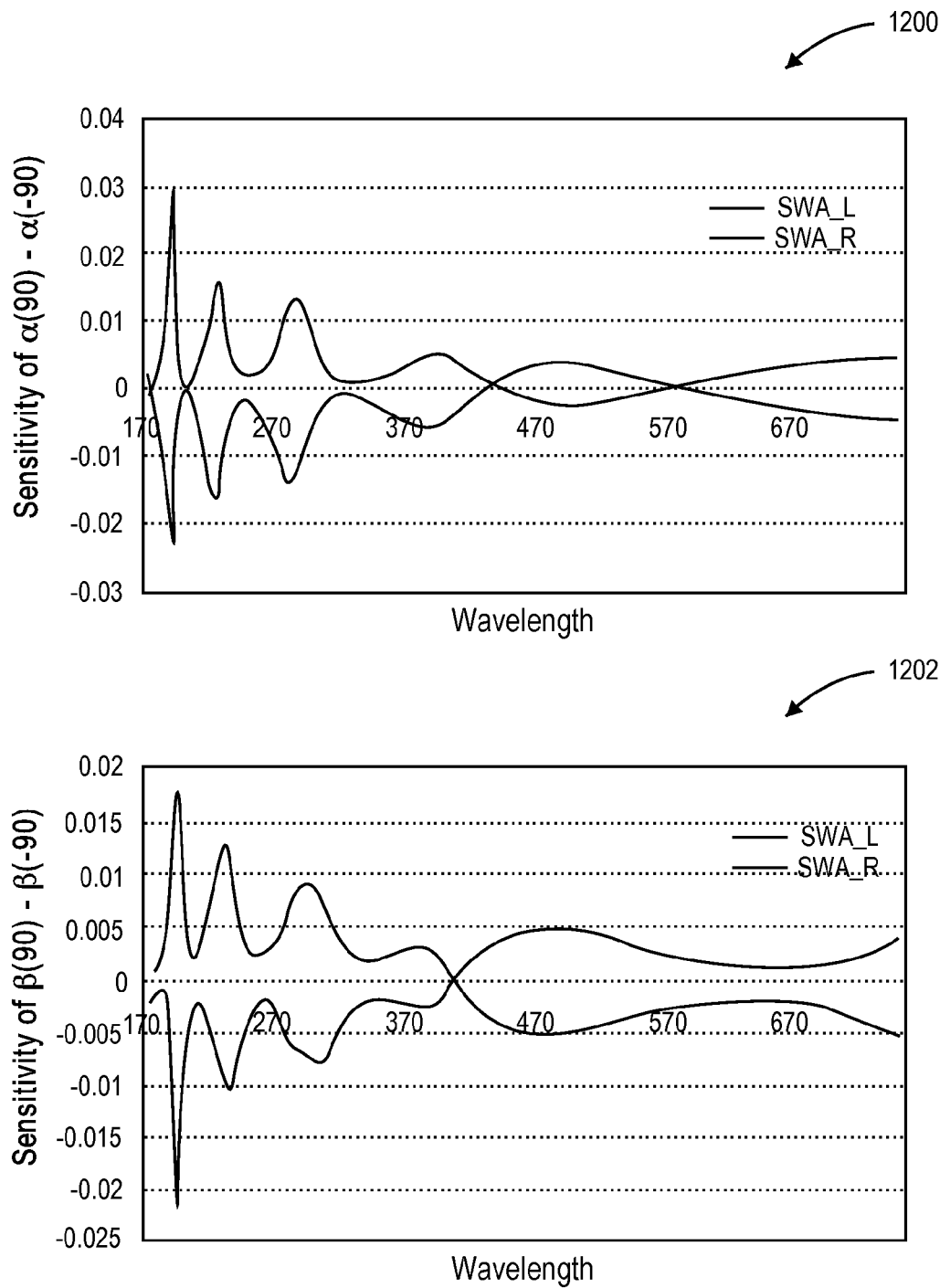
FIG. 12 includes plots 1200 and 1202 demonstrating the sensitivity of measurements of two wall angles at SWA_L=85° and SWA_R=86°, in accordance with an embodiment of the present invention.

By contrast, in one or more embodiments of the present invention, target 900 is measured at both 90 and −90 degree azimuth angles, as shown for target 1100 in FIG. 11. The difference of the two spectra of an asymmetric grating target 1100 is determined and used in a regression calculation. Thus, SWA_L and SWA_R can be more accurately determined due to the reduction of their correlation. The sensitivity of two wall angles at SWA_L=85° and SWA_R=86° is demonstrated in plots 1200 and 1202 of FIG. 12. The differential spectra may be used alone by itself in the regression or with one or more of the spectra measured at 0, 90, −90 degree azimuth angles to achieve the best sensitivity and the lowest correlation.

One or more embodiments of the present invention may be generalized in that, depending on the property of a measured structure, the differential spectra between measurement 1 with azimuth angle=$\phi_1$ and AOI=$\theta_1$, and measurement 2 with azimuth angle=$\phi_2$' and AOI=$\theta_2$, or multiple such differential spectra from pairs of measurements with different azimuth angles and/or AOI's is included in the regression in order to reduce the correlation and/or to increase the sensitivity of CD parameters. These differential spectra may be used in the regression by themselves or with other conventional non-differential spectra to achieve the best sensitivity and the lowest correlation.

Figure 13:
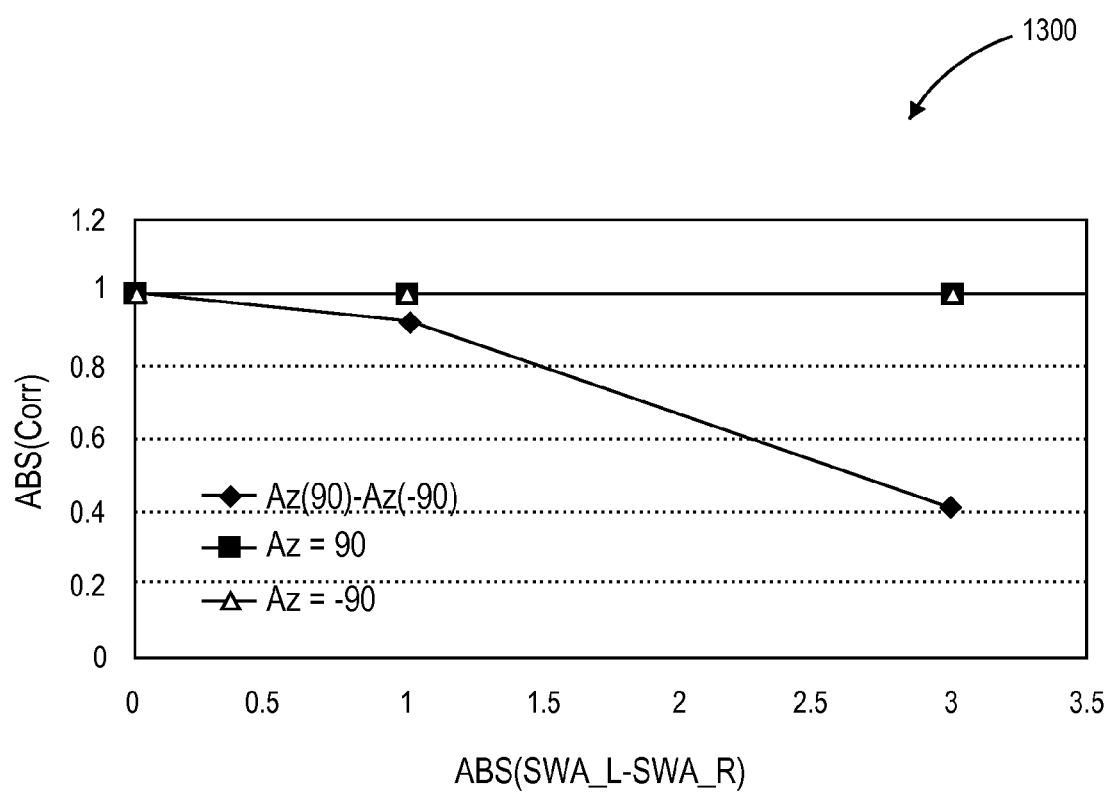
FIG. 13 is a plot 1300 demonstrating that the absolute value of correlation coefficient between the sensitivities of SWA_L and SWA_R reduces much more rapidly for the differential signal (denoted by "Az(90)-Az(−90)") than the regular signals (denoted by "Az=90" and "Az=−90"), in accordance with an embodiment of the present invention.

In accordance one or more embodiments of the present invention, an advantage of the above described approach is the ability to reduce the correlation of the same (or similar) types of CD parameters at different locations of asymmetric semiconductor device structures. In one embodiment, the absolute value of correlation coefficient between the sensitivities of SWA_L and SWA_R reduces much more rapidly for the differential signal (denoted by "Az(90)-Az(−90)") than the regular signals (denoted by "Az=90" and "Az=−90"), as shown in plot 1300 of FIG. 13.

In an embodiment, differential scatterometer signals are used with each spectrum computed by taking the difference of two signals measured at two different azimuth angles and/or two different angles of incidence in regression of semiconductor device critical dimensions in order to improve the accuracy of the critical dimension measurements. As semiconductor devices become more and more complex today, there are more and more asymmetric structures that rely on optical CD (OCD) metrology to monitor critical dimensions. The differential scatterometer signals may provide more asymmetry information about asymmetric structures than the conventional signals. These new signals may enable measurement of many asymmetric parameters that cannot be measured accurately today due to high parameter correlation or low parameter sensitivity. The new signals may also be used to greatly improve time-to-result on a number of asymmetric structures that would otherwise require workaround and/or trial-and-errors approaches.

Figure 14:
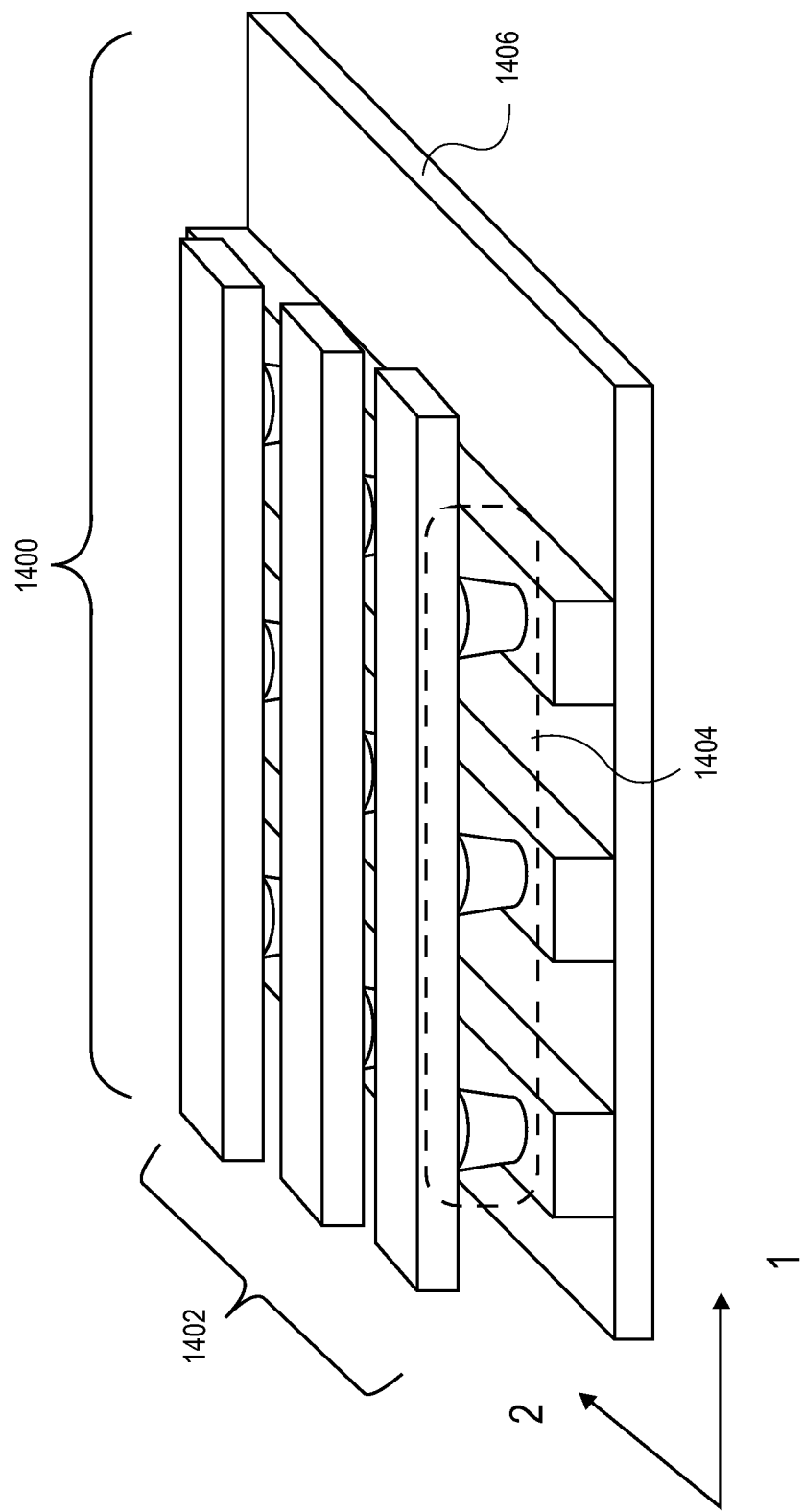
FIG. 14 represents a cross-sectional view of a structure having both a two-dimensional component and a three-dimensional component, in accordance with an embodiment of the present invention.

Embodiments of the present invention may be suitable for a variety of film stacks. For example, in an embodiment, a method for determining the asymmetry properties of CD profiles is performed for a film stack including an insulating film, a semiconductor film and a metal film formed on a substrate. In an embodiment, the film stack includes a single layer or multiple layers. Also, in an embodiment invention, an analyzed or measured grating structure includes both a three-dimensional component and a two-dimensional component. For example, the efficiency of a computation based on simulated diffraction data may be optimized by taking advantage of the simpler contribution by the two-dimensional component to the over all structure and the diffraction data thereof. FIG. 14 represents a cross-sectional view of a structure having both a two-dimensional component and a three-dimensional component, in accordance with an embodiment of the present invention. Referring to FIG. 14, a structure 1400 has a two-dimensional component 1402 and a three-dimensional component 1404 above a substrate 1406. The grating of the two-dimensional component runs along direction 2, while the grating of the three-dimensional component runs along both directions 1 and 2. In one embodiment, direction 1 is orthogonal to direction 2, as depicted in FIG. 14. In another embodiment, direction 1 is non-orthogonal to direction 2.

Figure 15:
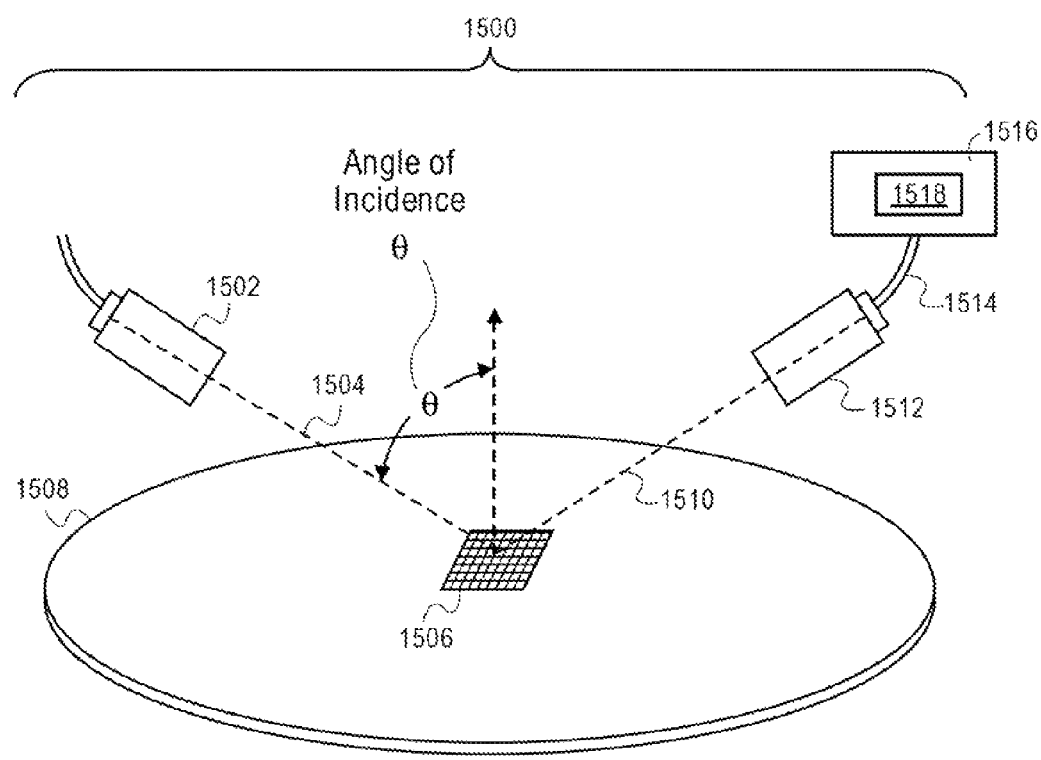
FIG. 15 is an architectural diagram illustrating the utilization of optical metrology to determine the profiles of structures on a semiconductor wafer, in accordance with an embodiment of the present invention.

FIG. 15 is an architectural diagram illustrating the utilization of optical metrology to determine the profiles of structures on a semiconductor wafer, in accordance with embodiments of the present invention. The optical metrology system 1500 includes a metrology beam source 1502 projecting a metrology beam 1504 at the target structure 1506 of a wafer 1508. The metrology beam 1504 is projected at an incidence angle θ towards the target structure 1506. The diffraction beam 1510 is measured by a metrology beam receiver 1512. The diffraction beam data 1514 is transmitted to a profile application server 1516. The profile application server 1516 compares the measured diffraction beam data 1514 against a library 1518 of simulated diffraction beam data representing varying combinations of critical dimensions of the target structure and resolution.

In accordance with an embodiment of the present invention, at least a portion of the simulated diffraction beam data is based on a difference determined for two or more azimuth angles. In accordance with another embodiment of the present invention, at least a portion of the simulated diffraction beam data is based on a difference determined for two or more angles of incidence. In one exemplary embodiment, the library 1518 instance best matching the measured diffraction beam data 1514 is selected. It is to be understood that although a library of diffraction spectra or signals and associated hypothetical profiles is frequently used to illustrate concepts and principles, the present invention applies equally to a data space including simulated diffraction signals and associated sets of profile parameters, such as in regression, neural network, and similar methods used for profile extraction. The hypothetical profile and associated critical dimensions of the selected library 1516 instance is assumed to correspond to the actual cross-sectional profile and critical dimensions of the features of the target structure 1506. The optical metrology system 1500 may utilize a reflectometer, an ellipsometer, or other optical metrology device to measure the diffraction beam or signal.

In order to facilitate the description of embodiments of the present invention, an ellipsometric optical metrology system is used to illustrate the above concepts and principles. It is to be understood that the same concepts and principles apply equally to the other optical metrology systems, such as reflectometric systems. In a similar manner, a semiconductor wafer may be utilized to illustrate an application of the concept. Again, the methods and processes apply equally to other work pieces that have repeating structures.

The present invention may be provided as a computer program product, or software, that may include a machine-readable medium having stored thereon instructions, which may be used to program a computer system (or other electronic devices) to perform a process according to the present invention. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., carrier waves, infrared signals, digital signals, etc.)), etc.

Figure 16:
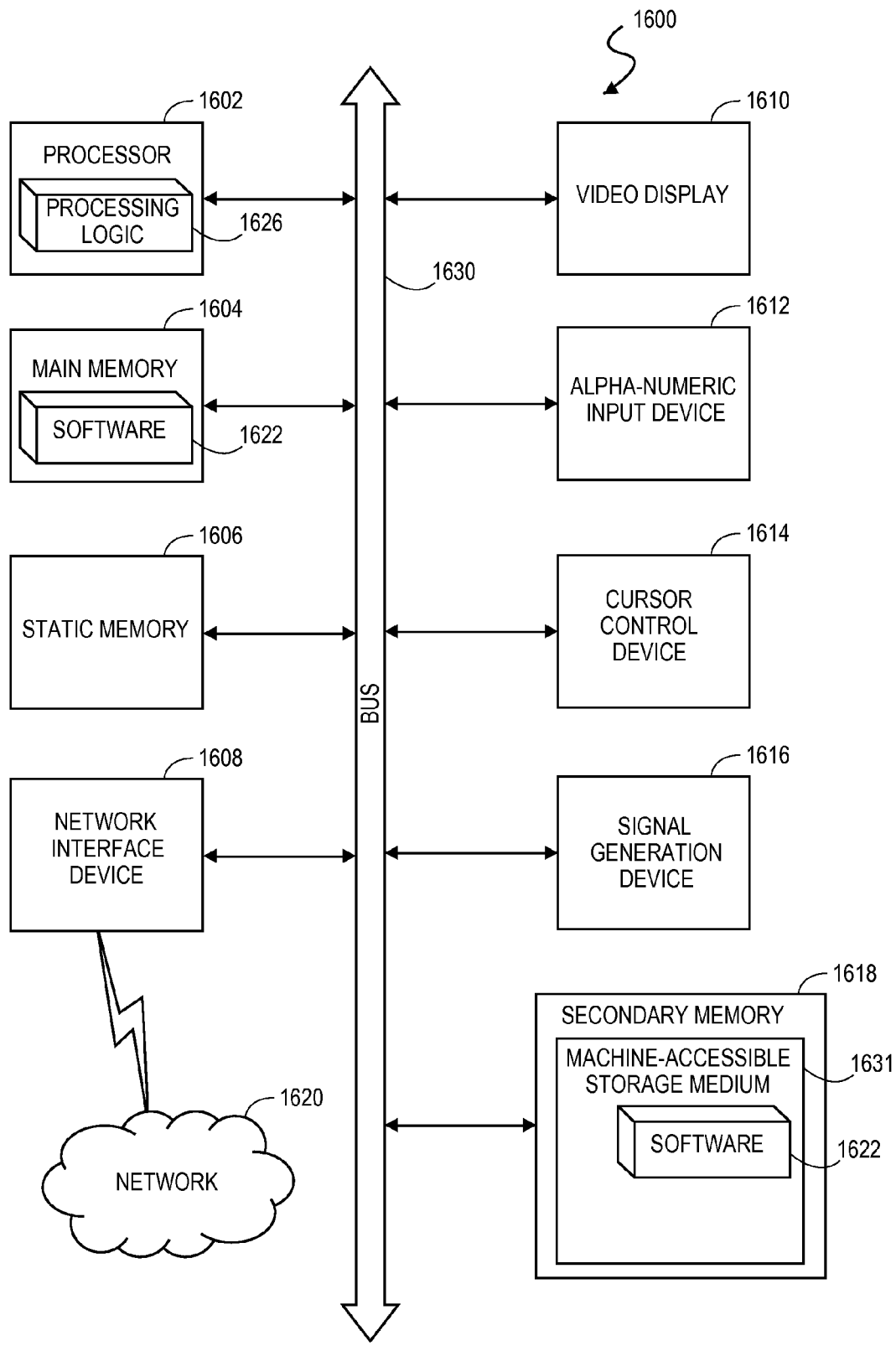
FIG. 16 illustrates a block diagram of an exemplary computer system, in accordance with an embodiment of the present invention.

FIG. 16 illustrates a diagrammatic representation of a machine in the exemplary form of a computer system 1600 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 1600 includes a processor 1602, a main memory 1604 (e.g., read-only memory (ROM), flash memory, dynamic random access memory (DRAM) such as synchronous DRAM (SDRAM) or Rambus DRAM (RDRAM), etc.), a static memory 1606 (e.g., flash memory, static random access memory (SRAM), etc.), and a secondary memory 1618 (e.g., a data storage device), which communicate with each other via a bus 1630.

Processor 1602 represents one or more general-purpose processing devices such as a microprocessor, central processing unit, or the like. More particularly, the processor 1602 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 1602 may also be one or more special-purpose processing devices such as an application specific integrated circuit (ASIC), a field programmable gate array (FPGA), a digital signal processor (DSP), network processor, or the like. Processor 1602 is configured to execute the processing logic 1626 for performing the operations discussed herein.

The computer system 1600 may further include a network interface device 1608. The computer system 1600 also may include a video display unit 1610 (e.g., a liquid crystal display (LCD) or a cathode ray tube (CRT)), an alphanumeric input device 1612 (e.g., a keyboard), a cursor control device 1614 (e.g., a mouse), and a signal generation device 1616 (e.g., a speaker).

The secondary memory 1618 may include a machine-accessible storage medium (or more specifically a computer-readable storage medium) 1631 on which is stored one or more sets of instructions (e.g., software 1622) embodying any one or more of the methodologies or functions described herein. The software 1622 may also reside, completely or at least partially, within the main memory 1604 and/or within the processor 1602 during execution thereof by the computer system 1600, the main memory 1604 and the processor 1602 also constituting machine-readable storage media. The software 1622 may further be transmitted or received over a network 1620 via the network interface device 1608.

While the machine-accessible storage medium 1631 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, solid-state memories, and optical and magnetic media.

In accordance with an embodiment of the present invention, a machine-accessible storage medium has instructions stored thereon which cause a data processing system to perform a method of determining an asymmetric property of a structure. The method includes measuring, for a grating structure, a first signal and a second, different, signal obtained by optical scatterometry. The method also includes determining a difference between the first signal and the second signal. The method further includes determining an asymmetric structural parameter of the grating structure based on a calculation using the first signal, the second signal, and the difference.

In one embodiment, the first signal and the second signal are measured at first and second azimuth angles, respectively, of the grating structure. In one embodiment, the first signal and the second signal are measured at first and second angles of incidence, respectively, of the grating structure. In one embodiment, the first signal and the second signal are measured at first and second polarizer/analyzer angles, respectively, of the grating structure. In one embodiment, the first signal and the second signal are measured for first and second measurement targets, respectively, of the grating structure. In one embodiment, the asymmetric structural parameter is a sidewall angle, and wherein the grating structure has a first sidewall with a first sidewall angle and a second sidewall with a second, different, sidewall angle. In one embodiment, the asymmetric structural parameter is one such as, but not limited to, top corner roundings, bottom footings, or critical dimension (CD) pitch shifts. In one embodiment, the grating structure is composed of a first material and further includes sidewall spacers composed of a second, different material, and wherein the asymmetric structural parameter is one such as, but not limited to, sidewall spacer width or sidewall spacer height. In another embodiment, the asymmetric structural parameter is a grating structure composed of a first material and further including left and right sidewall spacers composed of a second and a third different materials, respectively.

In one embodiment, the calculation is a regression calculation. In a specific embodiment, determining the structural parameter further includes simultaneously using one or more non-differential signals in the calculation, the one or more non-differential signals is one such as, but not limited to, azimuth angles, angles of incidence, polarizer/analyzer angles, and additional measurement targets. In one embodiment, the optical scatterometry is a technique such as, but not limited to, optical spectroscopic ellipsometry (SE), beam profile reflectometry (BPR), or enhanced ultra-violet reflectometry (eUVR). In one embodiment, the method further includes altering parameters of a process tool based on the asymmetric structural parameter by using a technique such as, but not limited to, a feedback technique, a feed-forward technique, and an in situ control technique.

It is to be understood that the above methodologies may be applied under a variety of circumstances within the spirit and scope of embodiments of the present invention. For example, in an embodiment, measurements described above are performed with or without the presence of background light. In an embodiment, a method described above is performed in a semiconductor, solar, light-emitting diode (LED), or a related fabrication process. In an embodiment, a method described above is used in a stand-alone or an integrated metrology tool. In an embodiment, a method described above is used in single- or multiple-measurement target regressions.

Thus, methods of determining asymmetric properties of structures have been disclosed. In accordance with an embodiment of the present invention, a method includes measuring, for a grating structure, a first signal and a second, different, signal obtained by optical scatterometry. A difference between the first signal and the second signal is then determined. An asymmetric structural parameter of the grating structure is determined based on a calculation using the first signal, the second signal, and the difference. In one embodiment, the first signal and the second signal are measured at first and second azimuth angles, respectively, of the grating structure. In one embodiment, the first signal and the second signal are measured at first and second angles of incidence, respectively, of the grating structure. In one embodiment, the first signal and the second signal are measured at first and second polarizer/analyzer angles, respectively, of the grating structure. In one embodiment, the first signal and the second signal are measured for first and second measurement targets, respectively, of the grating structure.

What is claimed is:

1. A method of determining and applying an asymmetric property of a structure, the method comprising:

measuring for a grating structure, a first signal and a second, different, signal obtained by optical scatterometry of the grating structure, the measurement of the first signal and second signal being performed by an optical metrology tool of an optical metrology system;

calculating with a processor of the optical metrology system:

a differential signal, the differential signal being a mathematical difference between the first signal and the second signal calculated by subtracting one of the first signal and the second signal from the other of the first signal and the second signal, and a value of an asymmetric structural parameter of the grating structure based on a calculation using the first signal, the second signal, and the calculated differential signal; and altering one or more parameters or settings for fabrication based at least in part on the calculated asymmetric structural parameter of the grating structure;

wherein the first signal and the second signal are measured according to one of the following:

the first signal and the second signal are measured at first and second azimuth angles, respectively, of the grating structure, the first signal and the second signal are measured for first and second angles of incidence, respectively, of the grating structure, the first signal and the second signal are measured at first and second polarizer/analyzer angles, respectively, of the grating structure, or the first signal and the second signal are measured for first and second measurement targets, respectively, of the grating structure.

2. The method of claim 1, wherein the calculation of the asymmetric structural parameter using the first signal, the second signal, and the calculated differential signal is a regression calculation.

3. The method of claim 2, wherein calculating the value of the asymmetric structural parameter further comprises simultaneously using one or more non-differential signals in the calculation, the one or more non-differential signals selected from the group consisting of signals determined using azimuth angles, angles of incidence, polarizer/analyzer angles, and additional measurement targets.

4. The method of claim 1, wherein the optical scatterometry performed by the optical metrology system is a technique selected from the group consisting of optical spectroscopic ellipsometry (SE), beam profile reflectometry (BPR), and enhanced ultra-violet reflectrometry (eUVR).

5. The method of claim 1, wherein calculating the asymmetric structural parameter of the grating structure based on the calculation using the first signal, the second signal, and the calculated differential signal comprises solving for Asymmetric Factor $$\eta = \sum_{i=1}^{n} d_i^2,$$

where $d_i$ is a differential signal with $i=1, \ldots, n$.

6. The method of claim 1, wherein calculating the value of the asymmetric structural parameter of the grating structure based on the calculation using the first signal, the second signal, and the calculated differential signal includes solving for $\eta = \sum_{i=1}^{n} \Delta\alpha^2(\lambda_i) + \sum_{i=1}^{n} \Delta\beta^2(\lambda_i)$.

7. A non-transitory machine-accessible storage medium having instructions stored thereon which cause a data processing system to perform a method of determining and applying an asymmetric property of a structure, the method comprising:

measuring, for a grating structure, a first signal and a second, different, signal obtained by optical scatterometry of the grating structure, the measurement of the first signal and second signal being performed by an optical metrology tool of an optical metrology system;

calculating with a processor of the optical metrology system:

a differential signal, the differential signal being a mathematical difference between the first signal and the second signal calculated by subtracting one of the first signal and the second signal from the other of the first signal and the second signal, and a value of an asymmetric structural parameter of the grating structure based on a calculation using the first signal, the second signal, and the calculated differential signal; and altering one or more parameters or settings for fabrication based at least in part on the calculated asymmetric structural parameter of the grating structure;

wherein the first signal and the second signal are measured according to one of the following:

the first signal and the second signal are measured at first and second azimuth angles, respectively, of the grating structure, the first signal and the second signal are measured for first and second angles of incidence, respectively, of the grating structure, the first signal and the second signal are measured at first and second polarizer/analyzer angles, respectively, of the grating structure, or the first signal and the second signal are measured for first and second measurement targets, respectively, of the grating structure.

8. The storage medium as in claim 7, wherein the calculation of the asymmetric structural parameter is a regression calculation.

9. The storage medium as in claim 8, wherein determining the structural parameter further comprises simultaneously using one or more non-differential signals in the calculation, the one or more non-differential signals selected from the group consisting of signals determined using azimuth angles, angles of incidence, polarizer/analyzer angles, and additional measurement targets.

10. The storage medium as in claim 7, wherein the optical scatterometry performed by the optical metrology system is a technique selected from the group consisting of optical spectroscopic ellipsometry (SE), beam profile reflectometry (BPR), and enhanced ultra-violet reflectrometry (eUVR).

11. The storage medium as in claim 7, wherein calculating the asymmetric structural parameter of the grating structure based on the calculation using the first signal, the second signal, and the calculated differential signal comprises solving for Asymmetric Factor $$\eta = \sum_{i=1}^{n} d_i^2,$$

where $d_i$ is a differential signal with $i=1, \ldots, n$.

12. The medium of claim 7, wherein calculating the value of the asymmetric structural parameter of the grating structure based on the calculation using the first signal, the second signal, and the calculated differential signal includes solving for $\eta=\Sigma_{i=1}{}''\Delta\alpha^2(\lambda_i)+\Sigma_{i=1}{}''\Delta\beta^2(\lambda_i)$.

13. A method of determining and applying an asymmetric property of a structure, the method comprising:
measuring for a grating structure, a first signal and a second, different, signal obtained by optical scatterometry of the grating structure, the measurement of the first signal and second signal being performed by an optical metrology tool of an optical metrology system;
calculating with a processor of the optical metrology system:
a differential signal, the differential signal being a mathematical difference between the first signal and the second signal calculated by subtracting one of the first signal and the second signal from the other of the first signal and the second signal, and
a value of an asymmetric structural parameter of the grating structure based on a calculation using the first signal, the second signal, and the calculated differential signal; and
altering one or more parameters or settings for fabrication based at least in part on the calculated asymmetric structural parameter of the grating structure;
wherein the asymmetric structural parameter is either:
a sidewall angle of the grating structure, and wherein the grating structure has a first sidewall with a first sidewall angle and a second sidewall with a second, different, sidewall angle, or
selected from the group consisting of top corner roundings, bottom footings, critical dimension (CD) pitch shifts of the grating structure.

14. A method of determining and applying an asymmetric property of a structure, the method comprising:
measuring for a grating structure, a first signal and a second, different, signal obtained by optical scatterometry of the grating structure, the measurement of the first signal and second signal being performed by an optical metrology tool of an optical metrology system;
calculating with a processor of the optical metrology system:
a differential signal, the differential signal being a mathematical difference between the first signal and the second signal calculated by subtracting one of the first signal and the second signal from the other of the first signal and the second signal, and
a value of an asymmetric structural parameter of the grating structure based on a calculation using the first signal, the second signal, and the calculated differential signal; and
altering one or more parameters or settings for fabrication based at least in part on the calculated asymmetric structural parameter of the grating structure;
wherein the grating structure is either:
composed of a first material and further comprises sidewall spacers composed of a second, different material, and wherein the asymmetric structural parameter is selected from the group consisting of sidewall spacer width and sidewall spacer height of the grating structure, or
composed of a first material and further comprises a first sidewall spacer composed of a second material and a second sidewall spacer composed of a third material and on an opposite sidewall from the first sidewall spacer, and wherein the asymmetric structural parameter is the composition difference between the second and third materials.

15. A non-transitory machine-accessible storage medium having instructions stored thereon which cause a data processing system to perform a method of determining and applying an asymmetric property of a structure, the method comprising:
measuring, for a grating structure, a first signal and a second, different, signal obtained by optical scatterometry of the grating structure, the measurement of the first signal and second signal being performed by an optical metrology tool of an optical metrology system;
calculating with a processor of the optical metrology system:
a differential signal, the differential signal being a mathematical difference between the first signal and the second signal calculated by subtracting one of the first signal and the second signal from the other of the first signal and the second signal, and
a value of an asymmetric structural parameter of the grating structure based on a calculation using the first signal, the second signal, and the calculated differential signal; and
altering one or more parameters or settings for fabrication based at least in part on the calculated asymmetric structural parameter of the grating structure;
wherein the asymmetric structural parameter is either:
a sidewall angle of the grating structure, and wherein the grating structure has a first sidewall with a first sidewall angle and a second sidewall with a second, different, sidewall angle, or
selected from the group consisting of top corner roundings, bottom footings, and critical dimension (CD) pitch shifts of the grating structure.

16. A non-transitory machine-accessible storage medium having instructions stored thereon which cause a data processing system to perform a method of determining and applying an asymmetric property of a structure, the method comprising:
measuring, for a grating structure, a first signal and a second, different, signal obtained by optical scatterometry of the grating structure, the measurement of the first signal and second signal being performed by an optical metrology tool of an optical metrology system;
calculating with a processor of the optical metrology system:
a differential signal, the differential signal being a mathematical difference between the first signal and the second signal calculated by subtracting one of the first signal and the second signal from the other of the first signal and the second signal, and
a value of an asymmetric structural parameter of the grating structure based on a calculation using the first signal, the second signal, and the calculated differential signal; and
altering one or more parameters or settings for fabrication based at least in part on the calculated asymmetric structural parameter of the grating structure;
wherein the grating structure is either:
composed of a first material and further comprises sidewall spacers composed of a second, different material, and wherein the asymmetric structural parameter is selected from the group consisting of sidewall spacer width and sidewall spacer height, or
composed of a first material and further comprises a first sidewall spacer composed of a second material and a second sidewall spacer composed of a third material and on an opposite sidewall from the first sidewall spacer, and wherein the asymmetric structural parameter is the composition difference between the second and third materials.

* * * * *